US00PP16381P3

(12) United States Plant Patent
Miyazaki

(10) Patent No.: US PP16,381 P3
(45) Date of Patent: Mar. 28, 2006

(54) ***PHLOX* PLANT NAMED 'SUNPHLOMINE'**

(50) Latin Name: *Phlox drummondii*
Varietal Denomination: Sunphlomine

(75) Inventor: Kiyoshi Miyazaki, Hikone (JP)

(73) Assignee: Suntory Flowers Limited, Tokyo (JP)

( * ) Notice: Subject to any disclaimer, the term of this patent is extended or adjusted under 35 U.S.C. 154(b) by 155 days.

(21) Appl. No.: 10/897,904

(22) Filed: Jul. 22, 2004

(65) Prior Publication Data

US 2006/0021102 P1 Jan. 26, 2006

(51) Int. Cl.
*A01H 5/00* (2006.01)

(52) U.S. Cl. ..... Plt./320
(58) Field of Classification Search ..... Plt./320
See application file for complete search history.

(56) References Cited

U.S. PATENT DOCUMENTS

PP12,070 P2 * 8/2001 van Gaalen ..... Plt./320
PP13,434 P2 * 12/2002 Cammarota ..... Plt./320
2002/0129420 P1 * 9/2002 Cammarota ..... Plt./320

OTHER PUBLICATIONS

UPOV ROM GTITM Computer Database, GTI Jouve Retrieval Software 2004/06 Citation for 'Sunphlomine'.*

Catalog for commercial producer in 2002–2003; Takii Seed Co., (3 pp); Published 2002 with partial English translation of p. 112.

Catalog for commercial breeder in 2000–2001; Sakata Seed Co., (3 pp); Published 2000 with partial English translation of p. 89.

* cited by examiner

*Primary Examiner*—Howard J. Locker
*Assistant Examiner*—W. C. Haas
(74) *Attorney, Agent, or Firm*—Christie, Parker & Hale, LLP

(57) ABSTRACT

Disclosed herein is a new and distinct variety of *Phlox* plant having an ascending habit and low plant height. The *Phlox* plant has abundant branching, and many of blooms, the whole plant remaining in bloom for a considerable period of time. The flowers are single, the upper side color of the corolla is vivid reddish purple and a deep purplish red at the center. The under side color of the corolla is deep purplish pink and the outside of the corolla tube is pale purplish pink. The plant exhibits a high tolerance to heat and resistance to disease.

2 Drawing Sheets

Botanical designation: *Phlox drummondii.*
Variety denomination: 'Sunphlomine'.

BACKGROUND OF THE VARIETY

The present invention relates to a new and distinct variety of *Phlox* plant originated from the crossing of a *Phlox* variety called '9Ph-17' (♀) with a commercial cultivar 'Palona Carmine' (unpatented PVP No.8900050 in United States) (♂).

*Phlox* are mainly late spring or summer flowering annuals or perennial, grown for terminal panicles or for a profusion of brightly colored flowers. However, there are only a few *Phlox* which can survive a hot and humid summer and can bloom continuously until autumn. Accordingly, this invention was aimed at obtaining a new variety having vivid reddish purple colored petals, together with good heat tolerance and a longer flowering period.

The female parent '9Ph-17' (unpatented) is a variety having a vigorous growth habit, abundant branching and good heat tolerance.

The male parent 'Palona Carmine' is a commercial cultivar.

In May 1999, crossing of a breeding line called '9Ph-17' as female parent with a cultivar 'Palona Carmine' as pollen parent was conducted at Yokaichi-shi, Shiga-ken, Japan. In January 2000, 50 seedlings were obtained from the crossing. The seedlings were grown in pots and tested, and then a single seedling was selected in view of the flower color, the good heat tolerance and a longer flowering period. The seedling was propagated by cutting and tested by flower potting and bedding from April 2001, at Yokaichi-shi, Shiga-ken, Japan. The botanical characteristics of the plant were then examined using a similar variety, 'Dolly Purple' (unpatented), for comparison. As a result, it was concluded that the *Phlox* plant is distinguishable from any other variety whose existence is known to us and is uniform and stable in its characteristics. The new variety of *Phlox* plant was named 'Sunphlomine'.

In the following description, the color information is in accordance with The R.H.S. Colour Chart of The Royal Horticultural Society, London, England.

SUMMARY OF THE VARIETY

This new variety is unlike any *Phlox* commercially available as evidenced by the following unique combinations of characteristics.

1. Ascending habit with short stem.
2. Having abundant branching with many blooms.
3. The flowers are single. The petal color is vivid reddish purple (R.H.S.78A) and a deep purplish red (R.H.S.71A) at the center.
4. The plant has a good tolerance to rain and heat.

The new variety 'Sunphlomine' differs from the male parent 'Palona Carmine' in the following points.

1. The stem color of 'Sunphlomine' is dark red (R.H.S.183A). That of 'Palona Carmine' is light yellow green (R.H.S.154D).
2. The number of primary branches of 'Sunphlomine' is more than that of 'Palona Carmine'.
3. The base color of corolla of 'Sunphlomine' is vivid reddish purple (R.H.S.78A). That of 'Palona Carmine' is strong reddish purple (R.H.S.78B).
4. The heat tolerance of 'Sunphlomine' is stronger than 'Palona Carmine'.

The new variety 'Sunphlomine' differs from the similar variety 'Dolly Purple' (PVP No.9300214 in United States) in the following points.

1. The stem color of 'Sunphlomine' is dark red (R.H.S.183A). That of 'Dolly Purple' is light yellow green (R.H.S.154D).
2. The diameter of corolla or 'Sunphlomine' is larger than that of 'Dolly Purple'.
3. The petal of 'Sunphlomine' is broader than that of 'Dolly Purple'.
4. The underside color of corolla of 'Sunphlomine' is deep purplish pink (R.H.S.68B). That of 'Dolly Purple' is pale purplish pink (R.H.S.69A).
5. The outside color of corolla tube of 'Sunphlomine' is pale purplish pink (R.H.S.69B). That of 'Dolly Purple' is vivid purplish red (R.H.S.71C).
6. The heat tolerance of 'Sunphlomine' is stronger than 'Dolly Purple'.

The new variety of *Phlox* plant 'Sunphlomine' was asexually reproduced by the use of cuttings at Yokaichi-shi, Shiga-ken, Japan, and the homogeneity and the stability thereof were confirmed.

The instant plant retains its distinctive characteristics and reproduces true to type in successive generations.

BRIEF DESCRIPTION OF THE PHOTOGRAPH

The accompanying photographs show, as nearly true as it is reasonably possible to make the same in color illustrations of this character, typical specimens of the new cultivar.

The depicted plants had been reproduced by the use of cuttings and were photographed June 2002 while growing outdoors in 20 cm pots at an age of approximately 3 months at Yokaichi-shi, Shiga-ken, Japan.

DESCRIPTION OF THE NEW VARIETY

Figure 1:
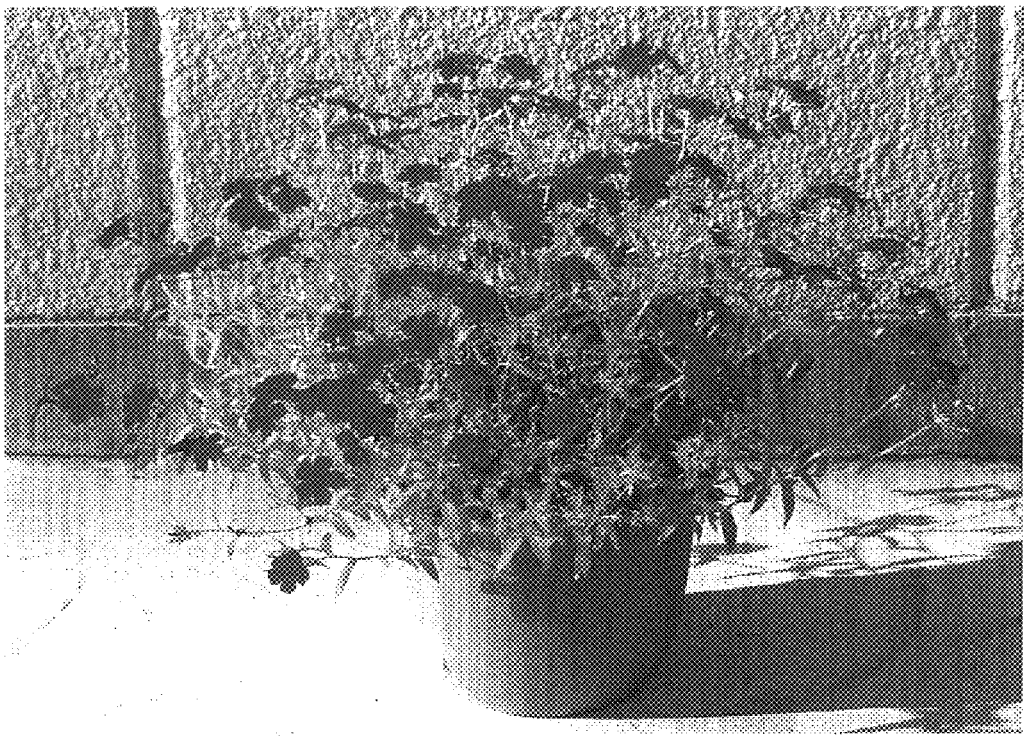
FIG. 1 illustrates an entire plant of the new variety while growing in a pot.
Figure 2:
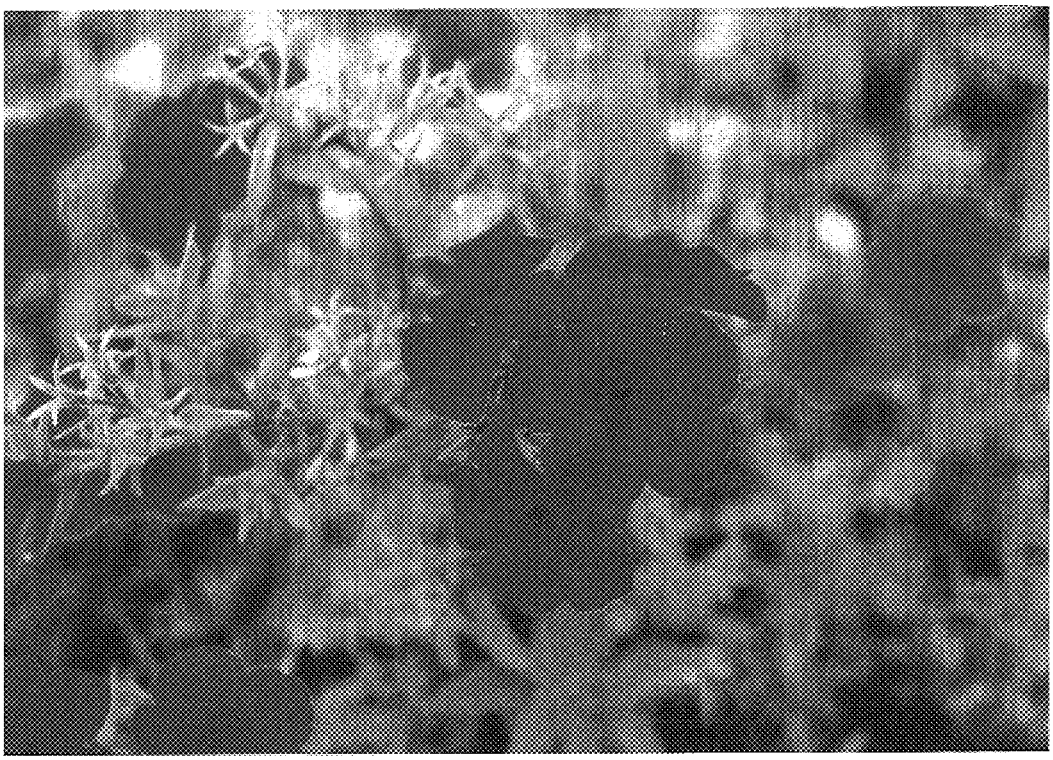
FIG. 2 illustrates a close view of the foliage and blossoms of the new variety.

The botanical characteristics of the new and distinct variety of *Phlox* plant named 'Sunphlomine' are set forth hereafter. The plants were observed as grown in typical outdoor conditions during June 2002 at Yokaichi-shi, Shiga-ken, Japan, at an age of approximately 3 months. The average day temperature is approximately 22° C. and the average night temperature is approximately 12° C.

Plant:

*Growth habit.*—Ascending.
*Plant height.*—Approximately 12 cm.
*Spreading area of plant.*—Approximately 30 cm.
*Blooming period.*—Early April to late October in the southern Kanto area, Japan. A typical flower commonly lasts approximately 5 days on the plant when experiencing a temperature of approximately 20° C.

Stem:

*Diameter.*—Approximately 1.7 mm.
*Pubescence.*—Present and typical of the species.
*Primary branching.*—Abundant, approximately 25.
*Internode length.*—Approximately 8.9 mm.
*Color.*—R.H.S. 183A (greyed-purple group).

Leaf:

*Phyllotaxis.*—Alternate.
*Whole shape.*—Lanceolate. The apex shape is acute, and the base shape is obtuse. The leaf margin shape is entire.
*Length.*—Approximately 2.8 cm.
*Width.*—Approximately 1.1 cm.
*Color.*—Upper side color is R.H.S. 137A (green group). Under side color is R.H.S. 146A (yellow-green group).
*Thickness.*—Approximately 0.2 mm.
*Pubescence.*—Present at upper side and under side.

Flower:

*Inflorescence.*—Cyme.
*Inflorescence length.*—Approximately 4.5 cm.
*Inflorescence width.*—Approximately 6.5 cm.
*Flower shape.*—Salverform.
*Corolla shape.*—Orbicular.
*Flower diameter.*—Approximately 2.9 cm.
*Flower depth.*—Approximately 1.5 cm.
*Petal width.*—Approximately 1.3 cm.
*Petal length from throat.*—Approximately 1.0 cm.
*Apex shape.*—Rounded cuspidate.
*Number of petal.*—5.
*Margin.*—Entire.
*Corolla tube diameter.*—Approximately 1.5 mm.
*Length of corolla tube.*—Approximately 1.5 cm.
*Upper petal surface color.*—Near R.H.S. 71A, petal base coloration is R.H.S. 78A.
*Lower petal surface color.*—Near R.H.S. 68B.
*Upper petal surface color* (*near the throat*).—Near R.H.S. 68B.
*Outside color of corolla tube.*—R.H.S. 69B (Red-purple group).
*Reproductive organs.*—1 normal pistil and 5 normal stamens. Color of pistil is R.H.S. 155B (white group). Color of stamen is R.H.S. 6B (yellow group).
*Pedicel.*—Approximately 1.0 mm in diameter and approximately 6.5 mm in length. Color of pedicel is near R.H.S. 146A.
*Calyx.*—Campanulate, 5 sepals fused at the base. Sepal length is approximately 7.5 mm, width is approximately 1.0 mm. Sepal shape is lanceolate. Upper and lower sepal surface color is near R.H.S. 146A. The calyx diameter is approximately 13 mm and the calyx depth is approximately 3.0 mm. The upper and lower sepal surfaces are smooth-textured.

The plant grows well at temperature up to 30° C.

The lower and upper temperatures for plant survival have not been evaluated. Disease resistance to pathogens common to *Phlox* has not been observed.

Seed production has not been observed.

This new variety of *Phlox* plant is most suitable for flower bedding, potting and planters. It is unnecessary to pinch of old blossoms to enhance the formation of new blossoms.

It is claimed:

1. A new and distinct variety of *Phlox* plant named 'Sunphlomine', substantially as herein illustrated and described.

* * * * *